(12) United States Patent
Stewart

(10) Patent No.: US 7,645,858 B2
(45) Date of Patent: Jan. 12, 2010

(54) METHOD OF PEPTIDE SYNTHESIS OF PEPTIDES CONTAINING A PROLINE RESIDUE OR HYDROXYPROLINE RESIDUE AT OR ADJACENT TO THE C-TERMINAL END OF THE PEPTIDE

(75) Inventor: Andrew Smith Johnstone Stewart, Haddington (GB)

(73) Assignee: Almac Sciences (Scotland) Limited, Edinburgh (GB)

( * ) Notice: Subject to any disclaimer, the term of this patent is extended or adjusted under 35 U.S.C. 154(b) by 0 days.

(21) Appl. No.: 10/566,601

(22) PCT Filed: Jul. 30, 2004

(86) PCT No.: PCT/GB2004/003312

§ 371 (c)(1),
(2), (4) Date: Mar. 9, 2006

(87) PCT Pub. No.: WO2008/014640

PCT Pub. Date: Feb. 17, 2005

(65) Prior Publication Data

US 2006/0241282 A1    Oct. 26, 2006

(30) Foreign Application Priority Data

Aug. 2, 2003   (GB) ................................. 0318205.2

(51) Int. Cl.
*C07K 1/04*    (2006.01)

(52) U.S. Cl. ...................... 530/334; 530/335; 530/336; 530/337; 530/402

(58) Field of Classification Search ...................... None
See application file for complete search history.

(56) References Cited

FOREIGN PATENT DOCUMENTS

| JP | 61 233699 A | 10/1986 |
| WO | WO 97/00960 A | 1/1997 |

OTHER PUBLICATIONS

Nokihara K et al.: "Studies on Peptides Having C-Terminal Proline Residues Using the Fmoc-chemistry," *Peptide Chemistry*, vol. 1994:32 (1995) pp. 245-248.

*Primary Examiner*—Anish Gupta
(74) *Attorney, Agent, or Firm*—Daniel A. Monaco; Drinker Biddle & Reath LLP

(57) ABSTRACT

A method for synthesizing a given peptide or its derivative which contains a proline residue or a proline derivative, at proximity to, or at, the C-terminal end of said peptide is provided. The method comprises a) synthesizing on a first resin a C-terminal portion of said peptide, or its derivative, comprising at least three successive amino acid residues or their derivatives, by successive coupling of selected amino acids, small peptides or their derivatives; b) cleaving the C-terminal portion from said first resin; c) reattaching said C-terminal portion to a second resin which is generally suitable for the synthesis of peptides but is unsuitable for the formation of peptides having a proline residue positioned at the C-terminal end of said peptide; and d) coupling selected amino acids, small peptides or derivatives to the C-terminal portion.

8 Claims, 3 Drawing Sheets

Wang resin

Diketopiperazine formation during synthesis of C-terminal proline containing peptides 2-chlorotrityl chloride resin

METHOD OF PEPTIDE SYNTHESIS OF PEPTIDES CONTAINING A PROLINE RESIDUE OR HYDROXYPROLINE RESIDUE AT OR ADJACENT TO THE C-TERMINAL END OF THE PEPTIDE

The chemical synthesis of peptides up to 40 residues is now routinely efficient and recent advances over the last 10 years has led to the synthesis of peptides and small proteins in the range of 40-150 residues. Efficient novel synthetic methodology and a wide array of resins which can be used for synthesis have contributed to this.

One particular resin, developed by Wang, S. S. *J. Amer. Chem. Soc.* 95, (1973), 1328, (see FIG. 1) has become the industry standard which has proven effective in the efficient synthesis of long peptides. There are however a number of problems with this resin which relate to the C-terminal amino acid. Firstly esterification of the resin with protected derivatives of cysteine and histidine can cause significant levels of racemisation which, of course, is highly undesirable. Further, whilst esterification with protected derivatives of proline is successful problems are encountered after an additional amino acid residue is added to form a dipeptide. Deprotection of the dipeptide in preparation for the coupling of the third amino acid gives a free amino dipeptide ester which often cyclises internally to form the free cyclic dipeptide (a diketopiperazine) shown in FIG. 2. The resultant loss of dipeptide is in most cases quantitative and renders use of the Wang resin unsuitable for the synthesis of C-terminal proline peptides. Moreover it has also been suggested that cyclisation also occurs when the penultimate C-terminal residue is a proline residue or one of its derivatives.

The use of the sterically hindered and extremely acid labile 2-chlorotrityl chloride resin (see FIG. 3) is recommended for the synthesis of C-terminal proline containing peptides (as the steric bulk inhibits diketopiperazine formation).

Experiments were carried out to synthesise medium length and long peptides where, due to the nature of the C-terminal residue, 2-chlorotrityl resin was used. The medium length peptide (about 30 residues) was HNP-1 where the C-terminal residue is cysteine The long peptide was guinea pig eotaxin, a 74 amino acid peptide, of which the C-terminal residue is proline.

Both experiments were unsuccessful. Low yields of both peptides were obtained and monitoring of the chain assembly showed a low coupling efficiency in both cases. By comparison with the situation when the HNP-1 peptide was synthesised on a Wang resin using a resin loading procedure that was reported to alleviate the problem of racemisation of C-terminal cysteine, the chain assembly proved excellent and the low yield obtained with the chlorotrityl resin was ascribed to some property of that resin.

One theory was that the extreme acid lability of this resin led to a premature cleavage of the peptide from the resin during chain assembly. The inventors varied the conditions of synthesis to try to eliminate the contact of the resin with acid species during chain assembly of guinea pig eotaxin but no improvement in yield was achieved. Another theory is that some property of the 2-chlorotrityl resin, e.g. swelling characteristics, renders it unsuitable and inefficient in the assembly of long peptides.

Thus 2-chlorotrityl resin appears only compatible with the synthesis of relatively short ( e.g. <20 residues) peptides. It has now been found that the problems associated with respect to a peptide containing a C-terminal proline on 2-chlorotrityl resin can be alleviated if the synthesis is carried out on the Wang resin.

SUMMARY OF THE INVENTION

Figure 1:
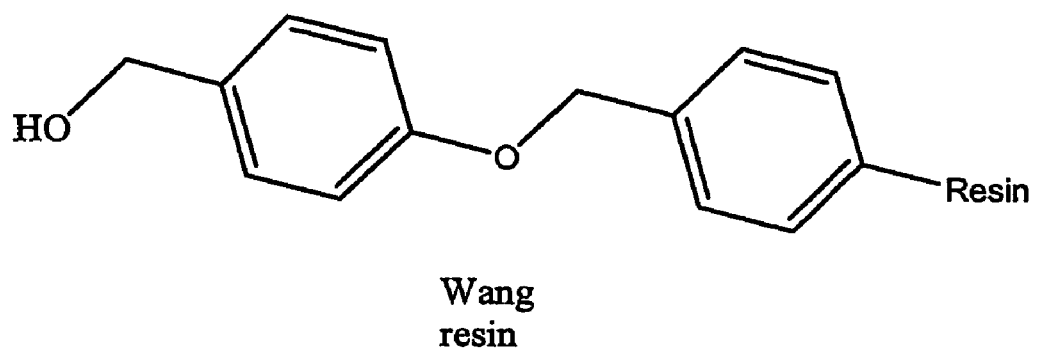
FIG. 1 shows molecular structure of the Wang resin linker.

The invention relates to a method for synthesis of a given peptide which contains a proline or one of its derivatives, at proximity to, or at, the C-terminus end of the peptide of interest. This method is particularly suitable for the synthesis of long peptides, for example peptides which have at least 20 amino acid residues or for peptides where synthesis is problematic on 2-chlorotritylchloride resin.

By the expression "proximity to" it is meant that the proline residue is positioned at the penultimate C-terminal position.

The expression "derivatives" is directed to a peptide, an amino acid or an amino acid residue which may differ from the corresponding peptide amino acid or residue by the substitution/addition of various substituents. It is usual in protein synthesis to use modified amino acids having protecting groups or which have been modified so as to be able to act as labels or tags or for other desirable purposes. For example, in the method of the present invention amino acid derivatives such as hydroxyproline or other proline derivatives could be used.

In a preferred embodiment, the method comprises the steps of:
a) synthesising on a first resin a C-terminal portion of said peptide, or its derivative, comprising at least three successive amino acid residues or their derivatives, by successive coupling of selected amino acids, small peptides or their derivatives, said first resin being suitable for the formation of peptides having a proline residue or a proline derivative positioned at, or at proximity of, the C-terminal end of said peptide;
b) cleaving the C-terminal portion thus obtained from said first resin;
c) reattaching said C-terminal portion to a second resin which is generally suitable for the synthesis of peptides but is unsuitable for the formation of peptides having a proline residue or a proline derivative positioned at, or at proximity of, the C-terminal end of said peptide; and
d) coupling selected amino acids, small peptides or derivatives to the C-terminal portion to obtain said given peptide.

Whilst peptides of any length can be synthesised using the method of the invention, the method is particularly suited for the synthesis of peptides having at least 20 amino acid residues or "long peptides". The method is particularly suitable for peptides having up to about 150 amino acid residues.

The method of the invention allows synthesis of peptides which were otherwise difficult to obtain quantitatively. Amongst such peptides which have a C-terminal proline residue and can be obtained using the method of the invention chemokines are of particular interest and particularly the human chemokines IP-10, BLC and MCP-2.

Advantageously, the first resin is chosen so that it does not lead to the formation of cyclic dipeptides and in particular to the formation of diketopiperazine compounds.

Step a) and/or d) of the method of the invention may be achieved by successive coupling of the predetermined amino acid residues, small peptides or their derivatives. This can be carried out using standard solid phase procedures which are well known. In these procedures, the α-amino group of the next selected amino acid or small peptide is protected using a protecting group and is added to the resin bearing the C-terminal portion of the peptide together with a coupling agent like diisopropylcarbodiimide (DIC) or dicyclohexylcarbodiimide (DCC). The α-amino protecting group is then removed by exposure to a suitable base which leaves the peptide bond intact and the next amino residue can then be added by repeating the above step. Such procedures are detailed for example in W. C. Chan and P. D. White, Fmoc Solid Phase Peptide Synthesis A Practical Approach, OUP 2000.

A preferred first resin for the formation of the C-terminal portion is the 2-chlorotrityl chloride resin or any similar resin which inhibits or minimises the formation of diketopiperazine.

A preferred resin to be used as the second resin for synthesis of a long peptide which can be used in the method of the invention is a resin having benzyl ester linker like the 4-(3-methoxy-4-(hydroxymethyl)phenoxymethyl) derivative of polystyrene-co-divinylbenzene which is marketed under the Trade Mark SASRIN™. A particularly preferred resin is a 4-Hydroxymethylphenoxymethyl resin known as Wang resin. Wang resins are well known and widely available.

Advantageously, the cleaving step from the first resin is achieved using a mild acid treatment, for example 20% trifluoroethanol in dichloromethane. This allows a fully protected (tri-) peptide moiety to be obtained. Thus, the C-terminal portion can be provided fully protected so it can be coupled directly onto the resin suitable for synthesis of a long peptide. The protective groups may be the standard protective groups usually used in Fmoc (9-fluorenylmethoxycarbonyl), Nsc (2-(4-nitrophenylsulfonyl)ethoxycarbonyl) or t-Boc (ter-butyloxycarbonyl) peptide synthesis.

Figure 2:
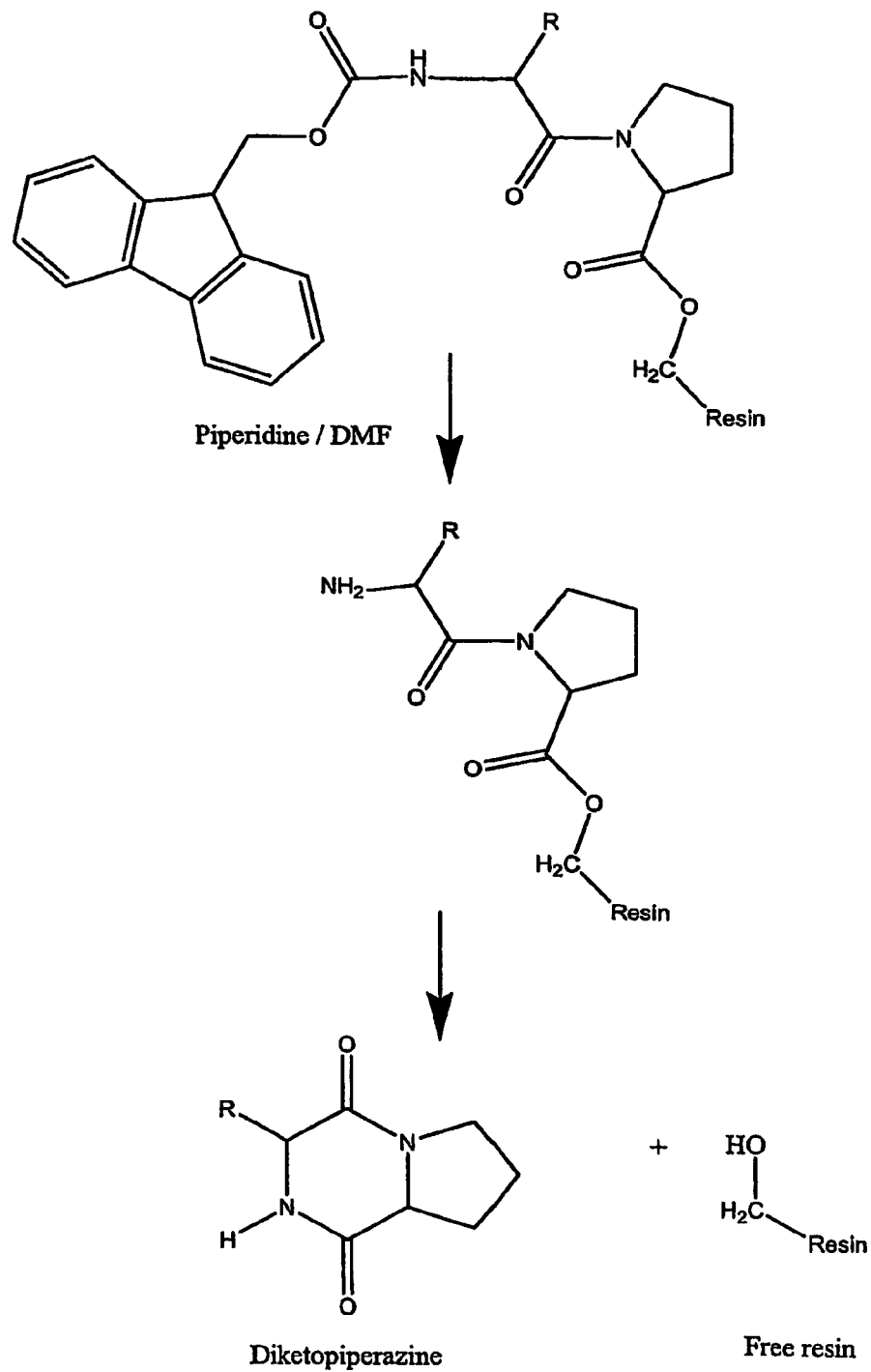
FIG. 2 shows formation of diketopiperazine.
Figure 3:
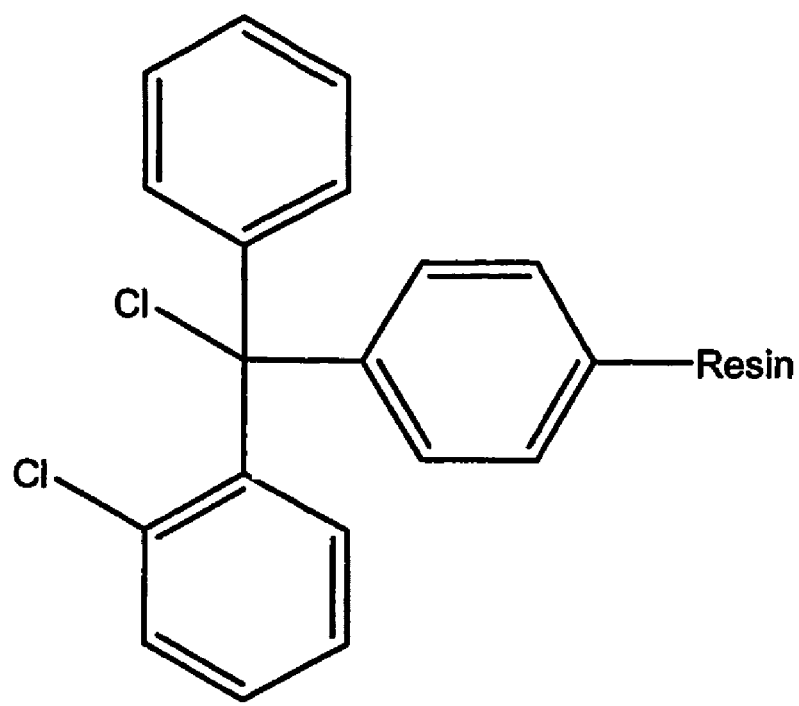
FIG. 3 shows molecular structure of the 2-chlorotrityl chloride resin linker.

The invention will now be described by way of example only, with respect to figures in which:

FIG. 1: shows molecular structure of the Wang resin linker.
FIG. 2: shows formation of diketopiperazine.
FIG. 3: shows molecular structure of the 2-chlorotrityl chloride resin linker.

EXAMPLE

The synthesis of guinea pig eotaxin, which contains a C-terminal proline residue, has been achieved using this resin exchange technique with an overall yield of 5 mg following purification and disulphide bond formation. When one considers that the same scale synthesis performed on a 2-chlorotrityl resin typically yields <1 mg overall, the advantages of the method according to the invention are clearly evident.

Any protein/peptide susceptible to diketopiperazine formation can be assembled using this described strategy. Polypeptides or proteins that contain proline or proline derivatives at, or adjacent to, the C-terminus are susceptible to diketopiperazine formation during assembly. The described approach will be extremely enabling for the synthesis of such peptides.

Synthesis of gp eotaxin Protected C-Terminal tripeptide on 2-chlorotrityl Resin (Fmoc-Thr(Bu$^t$)-Lys(Boc)-Pro-ClTrtR) (1)

Peptide synthesis was carried out on the ABI 430A peptide synthesiser. H-Pro-2-chlorotrityl resin (1 g, 0.49 mmol/g, Lot no. PrT-2, Nankai Hecheng Co. Ltd., China) was used in the reaction vessel. Nsc-Lys(Boc)-OH (503 mg, 1 mmol) was activated with HOCt (4ml, 1 mmol, GL Biochem, (Shanghai) Ltd. China) and DIC (4 ml, 1 mmol, Acros) for 15 mins then transferred to the reaction vessel and coupled for 30 mins. A second cartridge of Nsc-Lys(Boc)-OH was activated similarly and recoupled to the resin after draining the first solution.

Following capping of unreacted amino groups on the resin with acetic acid anhydride (0.5M in DMF, 10 ml) the Nsc group was removed with Deblock solution (1% DBU, 20% piperidine in DMF).

Fmoc-Thr(But)-OH (397 mg, 1 mmol, Applied Biosystems) was activated in the same manner and coupled to the resin for 30 mins followed by recoupling of the same amino acid as before. After coupling the resin was washed with DMF then DCM and dried under vacuum giving a yield of 1.21 g of (1).

The synthesis was repeated using a further gram of resin furnishing 1.18 g of the title resin. The resin batches were combined for further work.

Cleavage and Isolation of Fmoc-Thr(Bu$^t$)-Lys(Boc)-Pro-OH (2)

The peptide resin (1) was stirred in a solution of trifluoroethanol (20%) in DCM (50 ml) for 60 mins. The resin turned dark green. The solution was filtered and evaporated under reduced pressure to give an oil which was triturated with cold diethyl ether/hexane. The solvent was evaporated and fresh hexane added to yield a solid from which the solvent was again removed by evaporation. A white solid (400 mg, 0.55 mmol) was obtained. Mass spectroscopy Electrospray positive ion found 723.4, expected for $C_{39}H_{54}N_4O_9$ 722.4 kD.

Coupling of (2) to Wang Resin to give Fmoc-Thr(Bu$^t$)-Lys(Boc)-Pro-O-Wang Resin (3)

The protected tripeptide (2) (400 mg, 0.55 mmol) was dissolved in the minimum volume of DMF (<2 ml) and activated by the addition of DIC (86 μl, 0.55 mmol) and sonicated for 15 mins.

Wang resin (800 mg, 0.56 mmol/g, Lot no. W-34, Nankai Hecheng Co. Ltd., China) was swollen in the minimum volume of DMF until just freely mobile and dimethylamino pyridine (a few crystals) added. The activated peptide solution (2) was added and the coupling reaction sonicated for 4 h. The mixture was then filtered and the resin washed with DMF, DCM and diethyl ether successively. The resin was dried under vacuum to give a final yield of 1.0 g. The Fmoc loading test was carried out on the resin and a final loading of 0.162 mmol/g was determined. It was established using Izumiya test that the loading of the tripeptide onto the Wang resin was racemisation free.

Synthesis of gp eotaxin on Wang Resin

The synthesis of gp eotaxin was carried out using 500 mg, 0.081 mmol of resin (3). Standard coupling cycles using 1 mmol of amino acid (HOCt 2 ml, 1 mmol) and DIC (2 ml, 1 mmol) were carried out on the ABI synthesiser with the exception that:

a) the next amino acid Fmoc-Thr(Trt)-OH was coupled without a prior capping step on the resin and
b) the N-terminal amino acid Fmoc-His(Trt)-OH was coupled using HOBt 2 mmol in place of HOCt.

The final Fmoc group was retained on the resin as a purification tag.

Cleavage, Purification and Isolation of gp eotaxin

After chain assembly, the Fmoc-peptide was cleaved with EDT/H$_2$O/TIS/thioanisole/TFA (0.5/1.0/0.2/0.2/10 ml) at 0°

C. under nitrogen for 4 h. The resin was removed by filtration and peptide precipitated into cold ether and centrifuged. It was purified by G50 Sephadex gel filtration and HPLC and the amino terminal Fmoc group cleaved from the protein using 20% piperidine in $CH_3CN/H_2O$ (1:1). DTT was added to reduce the side chain of Cys residues and the cleaved Fmoc removed by gel filtration to give the pure, reduced peptide. This was folded in 50 mM Tris pH8.0, 5 mM GSH/0.5 mM GSSG, and monitored by HPLC. Folding took about a week to complete.

The folded peptide was purified by HPLC, to give the pure, folded peptide. (Electrospray mass spectrometry; Expected mass 8356.9 Da, found 8353.9 Da).

The invention claimed is:

1. A method for synthesizing a given peptide or its derivative, which peptide or derivative contains a proline residue or hydroxyproline residue, at or adjacent to the C-terminal end of said peptide, the method comprising the steps of:
    a) synthesizing on a first resin a C-terminal portion of said peptide, or its derivative, comprising successive coupling of a first amino acid as the C-terminal amino acid residue to the first resin and subsequently coupling at least two successive amino acids to said C-terminal amino acid residue, wherein said C-terminal amino acid residue or the amino acid residue adjacent thereto is a proline residue or a hydroxyproline residue, and said first resin is a 2-chlorotrityl chloride resin;
    b) cleaving the C-terminal portion thus obtained from said first resin;
    c) reattaching said C-terminal portion to a second resin, wherein said second resin is a Wang resin or a 4-(3-methoxy-4-(hydroxymethyl)phenoxymethyl) derivative of polystyrene-co-divinylbenzene; and
    d) coupling selected amino acids, small peptides or derivatives thereof to the C-terminal portion to obtain said given peptide or its derivative.

2. The method of claim 1 wherein said given peptide is a peptide which comprises at least 20 amino acid residues.

3. The method of claim 1 wherein said given peptide is a chemokine having a proline residue at the C-terminus thereof.

4. The method of claim 1, wherein said first resin is chosen so that it does not lead to the formation of a cyclic dipeptide.

5. The method of claim 1, wherein said second resin is a Wang resin.

6. The method of claim 1, wherein said given peptide comprises up to 150 amino acid residues.

7. The method of claim 1, wherein the cleaving step is achieved using a mild acid treatment.

8. The method of claim 1, wherein the C-terminal portion is fully protected so it can be attached directly onto the second resin.

* * * * *

UNITED STATES PATENT AND TRADEMARK OFFICE
CERTIFICATE OF CORRECTION

PATENT NO. : 7,645,858 B2  Page 1 of 1
APPLICATION NO. : 10/566601
DATED : January 12, 2010
INVENTOR(S) : Andrew Smith Johnstone Stewart It is certified that error appears in the above-identified patent and that said Letters Patent is hereby corrected as shown below:

On the title page, item (87), "W02008/014640" should read -- W02005/014640 --.

Signed and Sealed this

Fourth Day of May, 2010

David J. Kappos
*Director of the United States Patent and Trademark Office*